United States Patent [19]

Jouquey et al.

[11] Patent Number: 4,661,295

[45] Date of Patent: * Apr. 28, 1987

[54] NOVEL RADIOACTIVE ESTRADIENES

[75] Inventors: Alain Jouquey, Paris; Jean-Noël Veltz, Saint-Denis; Jean Salmon; Michel Mouren, both of Paris, all of France

[73] Assignee: Roussel Uclaf, Paris, France

[*] Notice: The portion of the term of this patent subsequent to May 8, 2001 has been disclaimed.

[21] Appl. No.: 620,454

[22] Filed: Jun. 14, 1984

[30] Foreign Application Priority Data

Jun. 14, 1983 [FR] France .................................. 83 09812

[51] Int. Cl.$^4$ ................................................ C07J 1/00
[52] U.S. Cl. .................................. 260/397.45; 540/25; 540/40
[58] Field of Search ..................................... 260/397.45

[56] References Cited

U.S. PATENT DOCUMENTS 4,447,424  5/1984  Teutsch et al. ................... 260/239.5

OTHER PUBLICATIONS

"Steroids", vol. 30, No. 2 (1977) pp. 169–177 and 267–273, articles by Kose K. et al, and Musey et al.

*Primary Examiner*—Elbert L. Roberts
*Attorney, Agent, or Firm*—Bierman & Muserlian

[57] ABSTRACT

Novel radioactive estradienes labelled with tritium of the formula

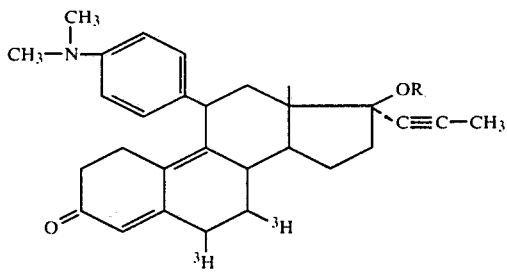

wherein $^3H$ is tritium and R is selected from the group consisting of hydrogen, alkyl of 1 to 6 carbon atoms and acyl of an organic carboxylic acid of 1 to 10 carbon atoms and the study and radioimmunological determination of non-radioactive 11β-(4-dimethylaminophenyl)-17α-(prop-1-ynyl)-Δ$^{4,9}$-estradiene-17β-ol-3-one and its metabolites in biological fluids and novel intermediates.

6 Claims, No Drawings

NOVEL RADIOACTIVE ESTRADIENES

STATE OF THE ART

U.S. Pat. No. 4,386,085 describes the non-radioactive compound, 11β-(4-dimethylaminophenyl)-17α-(prop-1-ynyl)-$\Delta^{4,9}$-estradiene-17β-ol-3-one, and U.S. Pat. No. 4,273,771 and French Pat. No. 2,414,515 describe other tritiated steroids of a different structure.

OBJECTS OF THE INVENTION

It is an object of the invention to provide the novel radioactive steroids of formula I and to provide a novel process and novel intermediates for their preparation.

It is another object of the invention to provide a novel method of studying and radio-immunologically determining of nonradioactive 11β-(4-dimethylaminophenyl)-17α-(prop-1-ynyl)-$\Delta^{4,9}$-estradiene-17β-ol-3-one and its metabolites in biological fluids.

These and other objects and advantages of the invention will become obvious from the following detailed description.

THE INVENTION

The novel compounds of the invention are radioactive estradienes labelled with tritium of the formula

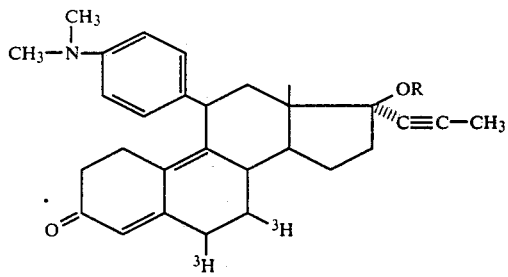

wherein $^3$H is tritium and R is selected from the group consisting of hydrogen, alkyl of 1 to 6 carbon atoms and acyl of an organic carboxylic acid of 1 to 10 carbon atoms.

Examples of R are hydrogen; alkyl of 1 to 6 carbon atoms such as methyl, ethyl, propyl, isopropyl, butyl, sec-butyl, tert-butyl, pentyl, iso-pentyl, sec-pentyl, tert-pentyl, neo-pentyl, hexyl, iso-hexyl, sec-hexyl and tert-hexyl; acyl such as formyl, acetyl, propionyl, butyryl, isobutyryl, valeryl, caproyl, benzoyl caprylyl, methoxycarbonyl and ethoxycarbonyl.

A preferred compound of the invention which will be hereinafter designated as compound A is 6,7-$^3$H-11β-(4-dimethylaminophenyl)-17α-(prop-1-ynyl)-$\Delta^{4,9}$-estradiene-17β-ol-3-one and its non-radioactive counter part will be designated hereinafter as compound B.

The novel process of the invention for the preparation of a compound of formula I comprises reacting a compound of the formula

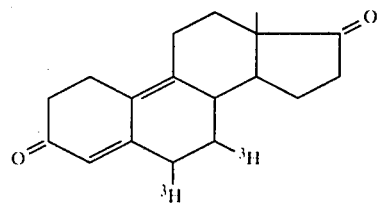

wherein $^3$H is tritium with a ketalizing agent to obtain a compound of the formula

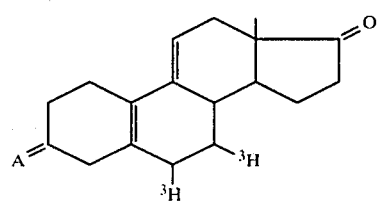

wherein A is an open or cyclic ketal, reacting the latter with a propynylating agent to obtain a compound of the formula

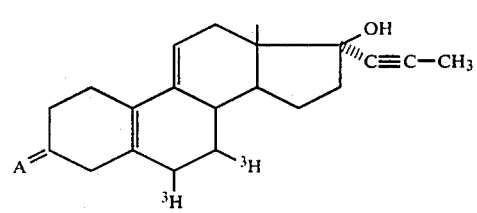

reacting the latter with an epoxidizing agent to obtain a compound of the formula

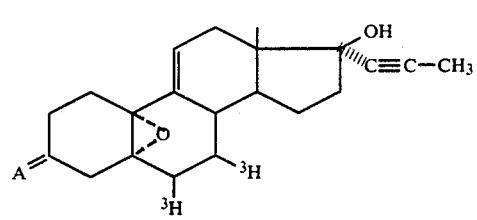

reacting the latter with a 4-dimethylamino-phenyl magnesium halide to form a compound of the formula

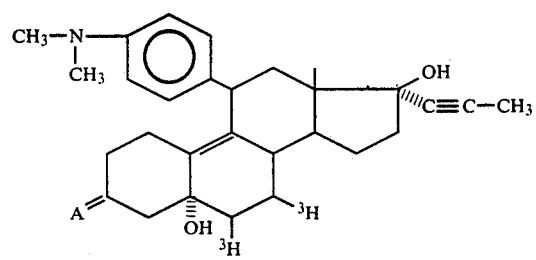

and hydrolyzing the latter to obtain the compound of formula I wherein R is hydrogen and optionally esterifying or etherifying the 17-hydroxy of the said compound.

In a preferred mode of the process, the ketalizing agent for the 3-keto group is an alkanol of 1 to 4 carbon atoms, or a glycol of 2 carbon atoms optionally substituted by one or two alkyls such as methyl, and the operation is carried out under inert atmosphere. The propynylating agent is propynyl magnesium bromide and the operation is carried out under an inert atmosphere, the epoxidizing agent is a peracid such as m-chloroperbenzoic acid or hydrogen peroxide in the presence of hexafluoroacetone hydrate and the operation is carried out under inert atmosphere; the 4-dimethylaminophenyl magnesium halide is the bromide and the operation is carried out under inert atmosphere and the product of formula VI is subjected to acid hydrolysis with hydrochloric acid and the operation is carried out under inert atmosphere.

The etherification or esterification of the 17-hydroxy of the product of formula I wherein R is hydrogen can be effected by the usual methods. The etherification can be effected, for example, with an etherification agent such as an alkyl or aryl halide or a dialkyl sulfate. The esterification can be effected, for example, with an esterification agent such as functional derivative of an acid such as a chloride of an acid or an anhydride.

According to a variation of the process of the invention the 3-ketone function of the product of formula II is blocked in the form of an open ketal with a ketalizing agent of the formula $R_1OH$ wherein $R_1$ is alkyl of 1 to 4 carbon atoms, the resulting product of the formula

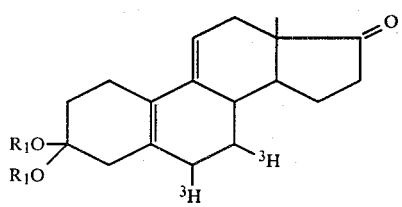

VII is reacted with a propynylating agent to obtain a product of the formula

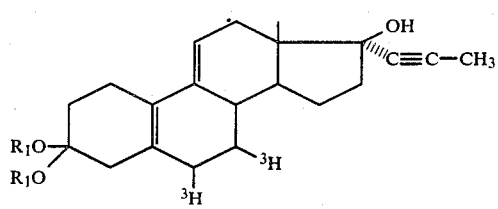

VIII transketalization of the ketal function is effected with a glycol of the formula $R_2CHOH\text{-}CHOHR_3$ in an acid medium to obtain a product of the formula

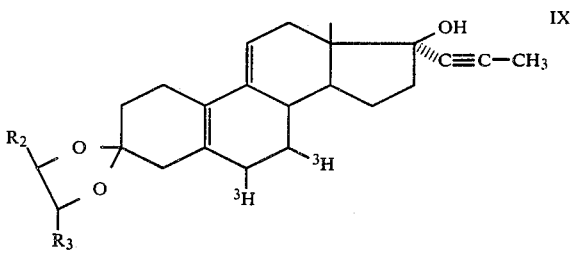

IX wherein $R_2$ and $R_3$ are individually selected from the group consisting of hydrogen and alkyl such as methyl, which is subjected to the action of an epoxidizing agent followed by reaction with a 4-dimethylaminophenyl magnesium halide, and finally hydrolysis to obtain the product of formula I.

In a preferred mode of the variation of the process, the ketalizing agent for the 3-ketone of formula II is methanol and the operation is carried out under an inert atmosphere, the propynylating agent is propynyl magnesium bromide and the operation is carried out under an inert atmosphere, the glycol for the transketalization of the ketone function of formula VIII is ethylene glycol and the operation is carried out under an inert atmosphere.

The choice of argon as an inert atmosphere is favored for executing the inventive process and a halide of 4-dimethylaminophenyl magnesium is reacted with a product of formula V in the presence of a cuprous salt, an alkanol as a ketalization agent for the 3-ketone is reacted in an acid medium such as a mixture of p-toluene sulfonic acid, hydrochloric acid, or hydrochloric acid-pyridine, and possibly in the presence of a dehydratant. A glycol is used as a ketalization agent to block the 3-keto group in the presence of a dehydratant, the propynylating agent is used in tetrahydrofuran, the epoxidizing agent is m-chloroperbenzoic acid, 4-dimethylaminophenyl magnesium bromide is used in tetrahydrofuran and in the presence of a cuprous salt, and the transketalization of the ketal function with a glycol is carried out in an acid medium, for example in pyridine-hydrochloride.

The invention also has as its subject the application of the products of formula I and particularly of product A for the study and the radio-immunological determination of product B and of its metabolites in biological fluids in man or animal. The invention also has as its subject a means for the study and the radio-immunological determination of the product B and its metabolites comprising a product of formula I and notably product A.

Product A, after its administration, can be followed in its evolution and its behaviour in the biological fluids during pharmacological and clinical studies. During these studies, product A enables particularly an easy specific determination of quantities of the order of several tens of picogrammes per ml. of biological fluid, without being obliged to recourse to methods of isolation and purification by chromatography before proceeding to the actual determination.

To study and determine by radio-immunological methods non-radioactive 11β-(4-dimethylamino-phenyl)-17α-(prop-1-ynyl)-Δ$^{4,9}$-estradiene-17β-ol-3-one or product B starting from this latter product, antigens are prepared by methods known per se, by combining it with bovine seric albumin (BSA) or human seric albumin (HSA). The resulting antigens serve for the development of anti-bodies when they are injected in an animal in the presence of an adjuvant and thus enable serums containing anti-bodies to be obtained. These anti-bodies then serve as receptors of radio-active products and/or non-radioactive products to wit as receptors of products of formula I and particularly of 6,7-$^3$H-11β-(4-dimethyl-aminophenyl)-17α-(prop-1-ynyl)-Δ$^{4,9}$-estradiene-17β-ol-3-one [product A] as well as of non-radioactive 11β-(4-dimethylaminophenyl)-17α-(prop-1-ynyl)-Δ$^{4,9}$-estradiene-17β-ol-3one [product B].

The presence of these anti-bodies is revealed by a product of formula I and particularly by product A. One then proceeds to the determination of product B by conventional radio-immunological methods such as those described by S. A. BERGSON et al, HORMONE, Vol. 4 p. 557 (1964) and ABRAHALI, J. of CHEM. ENDOCRINAL, METAB., Vol. 29 p. 886 (1969).

The products of formula I and particularly product A can furthermore be used for determining and localizing receptors of steroids such as receptors of glucocorticoids, of progestagens and androgens in the cells of the target tissues. The determination and localization of these receptors can be carried out by the usual methods such as those described by RAYNAUD et al., J. or STEROID BIOCHEM., Vol. 6 (1975) p. 615–622 and MOGUILEWSKY et al., J. of STEROID BIOCHEM., Vol. 12 (1980) p. 309–314.

The novel intermediates of the invention are 6,7-$^3$H-3,3-dimethoxy-17$\alpha$-(prop-1-ynyl)-$\Delta^{5(10),9(11)}$-estradiene-17$\beta$-ol, 6,7-$^3$H-3,3-ethylenedioxy-17$\alpha$-(prop-1-ynyl)-$\Delta^{5(10),9(11)}$-estradiene-17$\beta$-ol, 6,7-$^3$H-3,3-ethylenedioxy-5$\alpha$,10$\alpha$-epoxy-17$\alpha$-(prop-1-ynyl)-$\Delta^{9(11)}$-estrene-17$\beta$-ol and 6,7-$^3$H-3,3-ethylenedioxy-11$\beta$-(4-dimethylaminophenyl)-17$\alpha$-(prop-1-ynyl)-$\Delta^{9(11)}$-estrene-5$\alpha$,17$\beta$-diol.

In the following example there are described several preferred embodiments to illustrate the invention. However, it should be understood that the invention is not intended to be limited to the specific embodiments.

EXAMPLE 6,7-$^3$H-11$\beta$-(4-dimethylaminophenyl)-17$\alpha$-(prop-1-ynyl)-$\Delta^{4,9}$-estradiene-17$\beta$-ol-3-one

STEP A:
3,3-dimethoxy-6,7-$^3$H-$\Delta^{5(10),9(11)}$-estradiene-17-one

Under an inert atmosphere, 8 Ci or 40 mg of 6,7-$^3$H-$\Delta^{5(10),9(11)}$-estradiene-3,17-dione were introduced into 0.5 ml of acetone dimethylketal and then 50 $\mu$l of methanol containing 0.5% of acetyl chloride were added thereto. The mixture was left to stand for about 15 minutes, after which 20 $\mu$l of triethylamine were added followed by concentration under vacuum to obtain 3,3-dimethoxy-6,7-$^3$H-$\Delta^{5(10),9(11)}$-estradiene-17-one which was utilized as is for the following stage of the synthesis.

Thin layer chromatography on silica and elution with a 75-25 cyclohexane-ethyl acetate system gives Rf=0.25.

The starting product has been described in the publication J. SALMON: "Synthese et application of 17$\alpha$-methyltrienolone tritiée" (Symposium sur le progrès des techniques nucléaires en pharmacodynamie - Saclay 11–13 Mars 1970, Ed: MASSON,; G. VALETTE et Y. COHEN, p. 237–248).

STEP B:
3,3-dimethoxy-6,7-$^3$H-17$\alpha$-(prop-1-ynyl)-$\Delta^{5(10),9(11)}$-estradiene-17$\beta$-ol The product of Step A was added under an inert atmosphere to 0.5 ml of tetrahydrofuran and 0.5 ml of a 1M suspension of propynyl magnesium bromide in tetrahydrofuran was added. The mixture was stirred at ambient temperature for about 1 hour and 1 ml of a 10% aqueous solution of ammonium chloride was then added. After extraction with ethyl acetate, the organic phase was washed with water, and evaporated to dryness under reduced pressure to obtain 3,3-dimethoxy-6,7-$^3$H-17$\alpha$-(prop-1-ynyl)-$\Delta^{5(10),9(11)}$-estradiene-17$\beta$-ol which was utilized as is for the following stage of the synthesis. Thin layer chromatography on silica and elution with 75-25 cyclohexane-ethyl acetate system gives Rf=0.22.

STEP C:
3,3-ethylenedioxy-6,7-$^3$H-17$\alpha$-(prop-1-ynyl)-$\Delta^{5(10),9(11)}$-estradiene-17$\beta$-ol The product of Step B was taken up under an inert atmosphere in 1 ml of anhydrous glycol and 0.5 mg of pyridine hydrochloride was added thereto. The mixture was heated for about 30 minutes at 60° C. and after adding 2 ml of water, the mixture was extracted with ethyl acetate. The organic phase was washed with water, dried and evaporated to dryness to obtain 3,3-ethylenedioxy-6,7-$^3$H-17$\alpha$-(prop-1-ynyl)-$\Delta^{5(10),9(11)}$-estradiene-17$\beta$-ol Thin layer chromatography on silica and elution with 75-25 cyclohexane-ethyl acetate system gives Rf=0.2. The product was purified by high performance liquid chromatography on silica and was eluted with a cyclohexane-ethyl acetate with 0.06% water-triethylamine system (75:24:1) to obtain 2.44 Ci or 15 mg of the product.

STEP D:
3,3-ethylenedioxy-5$\alpha$,10$\alpha$-epoxy-6,7-$^3$H-17$\alpha$-(prop-1-ynyl)-$\Delta^{9(11)}$-estraene-17$\beta$-ol Under an inert atmosphere, 15 mg of the product of Step C were dissolved in 0.5 ml of methylene chloride and 10 mg of magnesium oxide were added. The mixture was cooled to −10° C., then with agitation, 12 mg of m-chloroperbenzoic acid were added, and agitation was maintained for about 1 hour at −10° C. 1 ml of a 0.2N aqueous solution of sodium thiosulfate was added followed by extraction with ethyl acetate. The organic phase was washed with water and evaporated to dryness under reduced pressure to obtain 3,3-ethylenedioxy-5$\alpha$,10$\alpha$-epoxy-6,7-$^3$H-17$\alpha$-(prop-1-ynyl)-$\Delta^{9(11)}$-estraene-17$\beta$-ol which is utilized as is for the following stage of the synthesis. Thin layer chromatography on silica and elution with a 75-25 cyclohexane-ethyl acetate system gives Rf=0.1.

STEP E:
3,3-ethylenedioxy-6,7-$^3$H-11$\beta$-(4-dimethylaminophenyl)-17$\alpha$-(prop-1-ynyl)-$\Delta^9$-estraene-5$\alpha$,17$\beta$-diol The product of Step D was dissolved under an inert atmosphere in 0.5 ml of tetrahydrofuran and 20 mg of cuprous iodide were added with stirring over about 20 minutes. Then, 0.5 ml of a 1M solution of 4-dimethylaminophenyl magnesium bromide in tetrahydrofuran was added and the mixture was maintained under agitation at ambient temperature for about 1 hour. The mixture was hydrolyzed with 0.5 ml of a 10% aqueous solution of ammonium chloride and 0.2 ml of a 0.2M aqueous solution of sodium thiosulfate. After extraction with ethyl acetate, the organic phase was washed with water and evaporated to dryness to obtain 3,3-ethylenedioxy-6,7-$^3$H-11$\beta$-(4-dimethylaminophenyl)-17$\alpha$-(prop-1-ynyl)-$\Delta^9$-estraene-5$\alpha$,17$\beta$-diol.

Thin layer chromatography on silica and elution with a 50-50 cyclohexane-ethyl acetate system gives Rf=0.22. The product was purified by high performance liquid chromatography on silica and eluted with a 70-30 cyclohexane-ethyl acetate with 0.06% water system containing 0.05% of triethylamine to obtain 1.08 Ci or 10 mg of the product.

STEP F:

6,7-³H-11β-(4-dimethylaminophenyl)-17α-(prop-1-ynyl)-Δ⁴,⁹-estradiene-3-one-17β-ol Under an inert atmosphere, 10 mg of the product of Step E were dissolved in 0.5 ml of methanol and 20 μl of concentrated hydrochloric acid were added thereto with stirring. The stirring was maintained for half-an-hour at ambient temperature and then 1 ml of ethyl acetate and 1 ml of N sodium hydroxide were added. The decanted organic phase was washed with water, dried and evaporated to dryness under reduced pressure to obtain crude 6,7-³H-11β-(4-dimethylaminophenyl)-17α-(prop-1-ynyl)-Δ⁴,⁹-estradiene-3-one-17β-ol. Thin layer chromatography on silica and elution with 50-50 cyclohexane-ethyl acetate system gives Rf=0.25. This product was purified by high performance liquid chromatography on silica, eluting with a 70-30 cyclohexane-ethyl acetate with 0.06% water system to obtain 6.3 mg of the product with a specific activity of 37.5 Ci mol⁻¹.

Various modifications of the products and processes of the invention may be made without departing from the spirit or scope thereof and it is to be understood that the invention is intended to be limited only as defined in the appended claims.

What we claim is:

1. A radioactive estradiene labelled with tritium of the formula

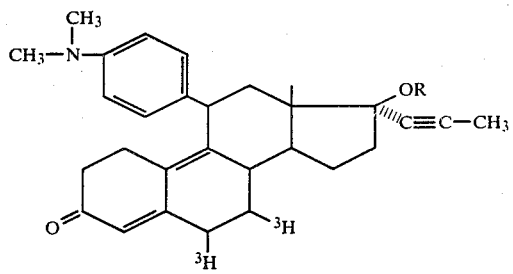

wherein ³H is tritium and R is selected from the group consisting of hydrogen, alkyl of 1 to 6 carbon atoms and acyl of an organic carboxylic acid of 1 to 10 carbon atoms.

2. A compound of claim 1 which is 6,7-³H-11β-(4-dimethylaminophenyl)-17α-(prop-1-ynyl)-Δ⁴,⁹-estradiene-17β-ol-3-one.

3. A compound selected from the group consisting of 6,7-³H-3,3-dimethoxy-17α-(prop-1-ynyl)-Δ⁵⁽¹⁰⁾,⁹⁽¹¹⁾-estradiene-17β-ol, 6,7-³H-3,3-ethylenedioxy-17α-(prop-1-ynyl)-Δ⁵⁽¹⁰⁾,⁹⁽¹¹⁾-estradiene-17β-ol, 6,7-³H-3,3-ethylenedioxy-5α,10α-epoxy-17α-(prop-1-ynyl)-Δ⁹⁽¹¹⁾-estrene-17β-ol and 6,7-³H-3,3-ethylenedioxy-11β-(4-dimethylaminophenyl)-17α-(prop-1-ynyl)-Δ⁹⁽¹¹⁾-estrene-5α,17β-diol.

4. A process for the preparation of a compound of claim 1 comprising reacting a compound of the formula

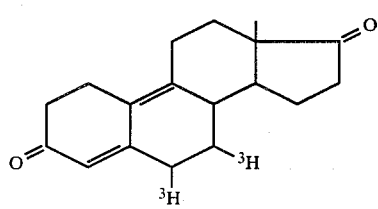

wherein ³H is tritium with a ketalizing agent selected from the group consisting of alkanol of 1 to 4 carbon atoms and optionally substituted glycol of 2 to 4 carbon atoms to obtain a compound of the formula

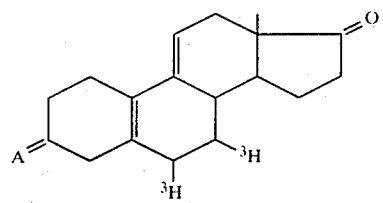

wherein A is an open or cyclic ketal, reacting the latter with a propynyl magnesium halide to obtain a compound of the formula

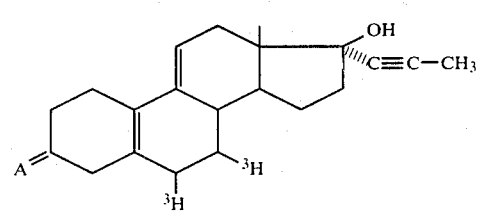

reacting the latter with an epoxidizing agent selected from the group consisting of peracids and hydrogen peroxide in the presence of hexafluoroacetone to obtain a compound of the formula

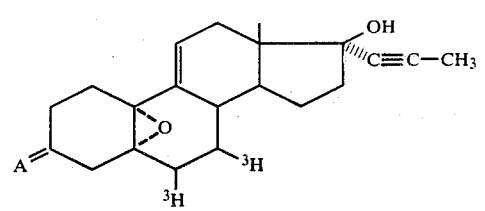

reacting the latter with a 4-dimethylamino-phenyl magnesium halide to form a compound of the formula

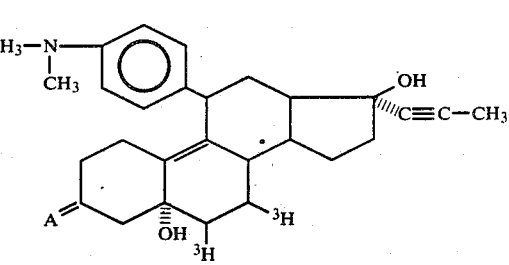

and hydrolyzing the latter to obtain the compound of formula I wherein R is hydrogen and optionally esterifying or etherifying the 17-hydroxy of the said compound.

5. In the study and radio-immunological determination of non-radioactive 11β-(4-dimethylaminophenyl)-17α-(prop-1-ynyl)-Δ⁴,⁹-estradiene-17β-ol-3-one and its metabolites in biological fluids of humans and warm-blooded animals, the improvement comprising using a compound of claim 1 in the method.

6. The method of claim 5 wherein the compound is 6,7-³H-11β-(4-dimethylaminophenyl)-17α-(prop-1-ynyl)-Δ⁴,⁹-estradiene-17β-ol-3-one.

* * * * *